United States Patent [19]

Miura et al.

[11] 4,213,962

[45] Jul. 22, 1980

[54] ARTIFICIAL MEDICAL MATERIAL WITH ANTICOAGULATIVE ACTIVITY

[75] Inventors: Yoshiharu Miura, 8-28, Katagiri-cho, Ibaraki, Osaka, Japan; Sadayoshi Aoyagi, Suita; Kazuhisa Miyamoto, Osaka, both of Japan

[73] Assignees: Yoshiharu Miura; Hideo Doi, both of Japan

[21] Appl. No.: 927,941

[22] Filed: Jul. 25, 1978

[30] Foreign Application Priority Data

Jul. 27, 1977 [JP] Japan .................................. 52-90673

[51] Int. Cl.² ..................... A61K 31/74; A61K 31/78; A61K 31/70; A61K 31/725
[52] U.S. Cl. .................................... 424/78; 424/81; 424/101; 424/180; 424/183
[58] Field of Search ................... 424/183, 81, 101, 94, 424/180, 78

[56] References Cited

U.S. PATENT DOCUMENTS

| 4,048,064 | 9/1977 | Clark | 424/183 |
| 4,073,723 | 2/1978 | Swank | 424/183 |

FOREIGN PATENT DOCUMENTS

| 52-36779 | 9/1977 | Japan | 424/183 |
| 49-38945 | 11/1977 | Japan | 424/183 |

OTHER PUBLICATIONS

Artificial Internal Organs (Jinko Zoki), vol. 1, No. 1, pp. 193 to 196, 1978.
Chem. Abst., vol. 80, 1974, 118771g, vol. 83, 1975, 39374p, vol. 84, 1976, 38917b, vol. 84, 1976, 119772c, vol. 85, 1976, 17351y.

Primary Examiner—Frederick E. Waddell
Attorney, Agent, or Firm—Berman, Aisenberg & Platt

[57] ABSTRACT

An artificial medical material with an anticoagulative activity which comprises a carrier material, and heparin and antithrombin III co-immobilized thereon by a per se conventional procedure.

13 Claims, No Drawings

ARTIFICIAL MEDICAL MATERIAL WITH ANTICOAGULATIVE ACTIVITY

The present invention relates to an artifical medical material with an anticoagulative activity. More particularly, it relates to an artificial medical material useful for prevention of blood coagulation and of formation of thrombus.

As well known, coagulation of blood is a phenomenon which is caused by formation of fibrin due to the action of thrombin to fibrinogen in blood. Such action of thrombin is inhibited by heparin and antithrombin III. Therefore, when it is necessary to prevent coagulation of blood and to maintain its fluidity, for example, in surgical operations, a large amount of heparin is administered so as to attain the object. However, the administration of heparin in a large amount may sometimes cause lethal side reactions, such as visceral bleeding. For overcoming such drawback, there has been recently proposed a method wherein heparin is immobilized on an appropriate carrier material, such as a water-insoluble high polymer, and blood is contacted therewith so that heparin catches thrombin without entering into blood, and blood coagulation is thus prevented.

As the result of the extensive study on prevention of blood coagulation and of formation of thrombus, it has now been found that an extremely high anticoagulative activity can be obtained when heparin and antithrombin III are immobilized together on a carrier material. In comparison with immobilization of heparin alone, the co-immobilization of these substances affords a much superior anticoagulative activity. Advantageously, a sufficient anticoagulative activity can be recognized even with small amounts of the anticoagulative substances, and a remarkable anticoagulative activity can be imparted even to a carrier material which is poor in functional groups.

The cooperation of heparin and antithrombin III to exert anticoagulative activity is well known. Since antithrombin III is essentially present in blood, it has been commonly thought that antithrombin III necessary for cooperation with heparin to exert anticoagulative activity can be naturally supplied from blood itself. Thus, the immobilization of heparin has been proposed and actually carried out, but its co-immobilization with antithrombin III has never been attempted. The said finding that the coimmobilized heparin and antithrombin III produce a much greater anticoagulative activity than the solely immobilized heparin is therefore entirely unexpected and surprising.

Recent study has revealed that the coagulation of blood proceeds through the action of the activated X factor (i.e. the Xa factor). Namely, it produces thrombin, whereby fibrin is separated, and blood coagulation takes place. Based on this mechanism, it is important for prevention of blood coagulation to inactivate the Xa factor, of which one unit can produce about 50 NIH units of thrombin. It has been found that the co-immobilization of heparin and antithrombin III is quite effective in inactivation of the Xa factor. Although antithrombin III itself can inactivate the Xa factor, the coexistence of heparin makes it possible to exert such inactivation effect instantaneously.

According to the present invention, there is provided an artificial medical material with an anticoagulative activity which comprises a carrier material, and heparin and antithrombin III co-immobilized thereon.

The characteristic feature of the invention resides in immobilization of heparin and antithrombin III in a coexistent state. Any characteristic feature is not present in the immobilization procedure itself, and the immobilization of the active substances may be effected by any technique conventionally adopted for immobilization of enzymes [cf. Ichiro Chibata et al.: "Koteika Koso (Immobilized Enzymes)", published by Kodansha (1975); "Seikagaku Jikken Koza (Series of Experiments in Biochemistry)", Vol. 5, Method for Investigation of Enzymes, Part VI, Immobilized Enzymes, pages 642–666 (1975); "Shin Jikken Kagaku Koza (Series of New Experimental Chemistry)", Vol. 20, Biological Chemistry I, Chapter I, Article 5, Immobilized Enzymes, pages 363–409 (1978); O. R. Zaborsky, "Immobilized Enzymes", Chemical Rubber Co., Press (1973); and the references cited in these books].

In production of the artificial medical material of the invention, any suitable procedure, such as the carrier linkage method (covalent linkage method, ion linkage method, physical adsorption method), the cross-linking method and the inclusion method, may be selected from various conventional methods for immobilization of enzymes. When the carrier-linkage method is adopted, for example, any conventional carrier material, such as a water-insoluble polymer material (e.g. cellulose, dextrane, agarose, polyacrylamide, polyvinyl alcohol, polyhydroxyethyl methacrylate,) is utilizable. Depending on the application or utilization form of the artificial medical material, an appropriate carrier material having suitable physical properties may be selected. By the immobilization of heparin and antithrombin III in a coexistent state, a sufficient anticoagulative activity can be obtained even with relatively small amounts of the active substances; therefore, even a carrier material while is poor in functional groups is still usable.

Depending on the procedure adopted for immobilization, activation of the carrier material may be sometimes required prior to its use. Such activation is also effected by any suitable conventional procedure for example by treatment with cyanogen bromide. There is no particular limitation of amounts of heparin and antithrombin III to be immobilized on the carrier material. Usually, 1 to 50 mg of heparin and 1 to 50 mg of antithrombin III are used per 1 g of the carrier material to obtain an artificial medical material having good anticoagulative activity. The proportion of the amounts of heparin and antithrombin III to be immobilized is also not particularly limited, but it is usually in the range of 1:1 to 10:1 (weight ratio). Though heparin and antithrombin III may be separately immobilized in successive steps, simultaneous immobilization is more advantageous in respect of simplicity of operations.

The artificial medical material of the invention may be prepared into any suitable form, such as powder, plate or tube depending on the physical properties of the carrier material. When blood is contacted with this medical material, thrombin and other elements are readily caught thereby and coagulation of blood is thus prevented.

The thrombin caught by the artificial medical material can be readily released therefrom, for example, by washing with an aqueous solution of acetic acid so that the ability for catching thrombin of the artificial medical material is recovered.

The present invention will be hereinafter explained further in detail by the following Examples and Reference Examples.

EXAMPLE 1

(A) Agarose (Sepharose 4B) (40 ml) (dry weight, about 1 g) is suspended in water (100 ml), and a 5 to 10 N NaOH aqueous solution is added thereto under stirring to make a pH value of 11 to 12. To this suspension, a BrCN solution (4–24 g/80–480 ml) is added while keeping the pH value of 11 to 12 with addition of the said NaOH aqueous solution until lowering of the pH value is not observed. During the reaction, the temperature of the reaction solution is kept to about 20° C. with addition of ice. The reaction is completed in 8 to 12 minutes. After completion of the reaction, the reaction mixture is immediately filtered through a glass filter, and the filtrate is washed with cold water (1 liter) to eliminate excess BrCN, whereby activated agarose is obtained.

(B) Activated agarose (500 mg) is suspended in a 0.1 M $NaHCO_3$ aqueous solution (5 ml), and a solution of heparin (100 mg) and antithrombin III (12.5 mg) in a 0.1 M $NaHCO_3$ aqueous solution (10 ml) is added thereto. The resultant mixture is stirred at 4° C. overnight. For blocking excess active groups in activated agarose, a 1 M ethanolamine aqueous solution (pH 8.0) (10 ml) is added, and after stirring at 4° C. for 1 hour, the reaction mixture is washed with a 2 M NaCl aqueous solution and a 0.15 M NaCl aqueous solution successively to obtain a heparin-antithrombin III-immobilized material (hereinafter referred to as "I-ATIII-HEP") in which 20 mg of heparin and 5 mg of antithrombin III are immobilized per 200 mg of activated agarose.

In the same manner as above, a heparin-immobilized material (hereinafter referred to as "I-HEP") in which 20 mg of heparin is immobilized per 200 mg of activated agarose and an antithrombin III-immobilized material (hereinafter referred to as "I-ATIII") in which 5 mg of antithrombin III is immobilized per 200 mg of activated agarose are obtained. Antithrombin III does not exhibit an anticoagulative activity unless immobilized under the protective action of heparin; therefore, in the preparation of the latter material, acetylated heparin in a 8-fold amount to antithrombin III is incorporated into the reaction system so as to protect the activity of antithrombin III and to immobilize it alone on activated agarose.

For preparation of a control, activated agarose is treated in the same manner as above but not using heparin nor antithrombin III.

(C) Citrated plasma (0.2 ml) (a supernatant obtained by centrifuging a mixture of blood and a 3.8% sodium citrate aqueous solution (9:1 by volume) at 3000 rpm for 15 minutes) is placed into a glass-made small test tube and warmed at 37° C., and a designed amount of an immobilized material is added thereto. Immediately thereafter, a 1/40 M calcium chloride aqueous solution (0.2 ml) is added, and the test tube is mildly shaken in an incubator at 37° C. The time required for coagulation of plasma is determined. The results are shown in Table 1.

Table 1

| Immobilized material | Coagulation time (sec.) | |
|---|---|---|
| | Amount of immobilized material used (1 mg) | Amount of immobilized material used (2.5 mg) |
| Control | 190 | 120 |
| I-HEP | 205 | 370 |
| I-ATIII | 225 | 550 |
| I-ATIII-HEP | 1200 | >24 hours |

From this table, it is understood that I-ATIII-HEP remarkably prolongs the time for blood coagulation in comparison with I-HEP or I-ATIII.

EXAMPLE 2

(A) Polyhydroxyethyl methacrylate (hereinafter referred to as "Poly-HEMA") (100 mg) is washed with water and immersed into a 0.1 M $Na_2CO_3$ aqueous solution (pH 11.0) overnight. The thus swelled substance is suspended in the said $Na_2CO_3$ solution, and the pH value is adjusted to 11.5 to 12.0 by the addition of a 1 N NaOH aqueous solution, the total volume of the mixture being made 20 ml. Under stirring, a BrCN solution (20–1000 mg/20 ml; adjusted to pH 11.5 to 12.0 with a 1 N NaOH aqueous solution) is added, and the reaction is carried out at about 10° C. for 30 minutes under a pH value of 11.5 to 12.0. After completion of the reaction, the reaction mixture is filtered by a glass filter and then washed with a 0.1 M $NaHCO_3$ aqueous solution repeatedly to obtain activated Poly-HEMA.

(B) Activated Poly-HEMA (100 mg) is suspended in a 0.1 M $NaHCO_3$ aqueous solution (2 ml), and a solution of heparin (20 mg) and antithrombin III (2 mg) in a 0.1 M $NaHCO_3$ aqueous solution (3 ml) is added thereto. The resultant mixture is stirred at 4° C. overnight. For blocking excess active groups in activated Poly-HEMA, a 1 M ethanolamine aqueous solution (pH 8.0) (1 ml) is added, and after stirring at 4° C. for 1 hour, the reaction mixture is washed with a 2 M NaCl aqueous solution and a 0.15 M NaCl aqueous solution successively to obtain a heparin-antithrombin III-immobilized material (hereinafter referred to as "I'-ATIII-HEP").

In the same manner as above, a heparin-immobilized material in which 2 mg of heparin is immobilized per 100 mg of activated Poly-HEMA (hereinafter referred to as "I'-HEP") and an antithrombin III-immobilized material in which 2 mg of antithrombin III is immobilized per 100 mg of activated Poly-HEMA (hereinafter referred to as "I'-ATIII") are prepared. Antithrombin III does not exhibit an anticoagulative activity unless immobilized under the protective action of heparin; therefore, in the preparation of the latter material, acetylated heparin in a 8-fold amount to antithrombin III is incorporated into the reaction system so as to protect the activity of antithrombin III and to immobilize it alone on activated Poly-HEMA.

For preparation of a control, activated Poly-HEMA is treated in the same manner as above but not using heparin nor antithrombin III.

(C) Citrated plasma (0.2 ml) (a supernatant obtained by centrifuging a mixture of blood and a 3.8% sodium citrate aqueous solution (9:1 by volume) at 3000 rpm for 15 minutes) is placed into a glass-made small test tube and warmed at 37° C., and the immobilized material (1.25 mg) is added thereto. Immediately thereafter, a 1/40 M calcium chloride solution (0.2 ml) is added, and the test tube is mildly shaken in an incubator at 37° C. The time required for coagulation of plasma is determined. The results are shown in Table 2.

Table 2

| Immobilized material | Coagulation time (sec.) |
|---|---|
| Control | 120 |
| I'-HEP | 170 |
| I'-ATIII | 150 |
| I'-ATIII-HEP | 250 |

From this table, it is understood that I'-ATIII-HEP remarkably prolongs the time for blood coagulation in comparison with I'-HEP or I'-ATIII.

EXAMPLE 3

The same procedure as in Example 2 is effected but using polyvinyl alcohol in place of Poly-HEMA. The thus obtained heparin-antithrombin III-immobilized polyvinyl alcohol is proved to have a much more remarkable anticoagulative activity in comparison with an immobilized polyvinyl alcohol in which heparin or antithrombin alone is immobilized.

EXAMPLE 4

Each of I-ATIII-HEP, I-ATIII and I-HEP obtained in Example 1 (each 10 mg) is suspended in a 0.15 M NaCl aqueous solution (0.2 ml). To the I-ATIII-HEP suspension, a 0.15 M NaCl aqueous solution (0.1 ml) is added. To the I-ATIII suspension, a heparin solution (165 units/ml) (0.1 ml), and to the I-HEP suspension, an antithrombin III solution (1 mg/ml) (0.1 ml) are added, respectively. A thrombin solution (in the system of measurement of coagulation time, 0.1 ml of this solution shows an activity of 10 seconds in coagulation time) (0.2 ml) is further added thereto, and the mixture is shaken for 30 minutes in an incubator at 37° C. to effect the reaction. A part (0.1 ml) of the supernatant which contains remaining thrombin is taken out and added to an acacia solution (0.2 ml) warmed at 28° C. (a mixture of a 15% acacia saline solution, a 1% chlorine saline solution, an imidazole buffer and a saline solution (2:1:1:5 by volume)). After stirring, the mixture is allowed to stand still in a constant temperature tank of 28° C. for 3 minutes. A standard fibrinogen solution (0.1 ml) (obtained by dissolving commercially available fibrinogen in a 0.15 M NaCl aqueous solution and, after adjusting the pH value to 7.2 with a 0.5 M $Na_2HPO_4$ aqueous solution, diluting with a 0.15 M NaCl aqueous solution to make a concentration of 1%) is added thereto, and the coagulation time is measured so as to determine the remaining thrombin activity in the supernatant. Separately, activated agarose not subjected to the immobilization of heparin and antithrombin III, which is used as a control, is suspended in a 0.1 M NaCl aqueous solution (0.2 ml), and an antithrombin III solution (1 mg/ml) (0.1 ml) is added thereto. Then, the same procedure as above is carried out. The results are shown in Table 3.

Table 3

| Anticoagulative system | Coagulation time (sec.) |
|---|---|
| Control + Antithrombin III solution | 70 |
| I-HEP + Antithrombin III solution | 130 |
| I-ATIII + Heparin solution | 160 |
| I-ATIII-HEP + 0.15 M NaCl solution | 350 |

From this table, it is understood that the heparin-antithrombin III-immobilized system shows a much stronger anticoagulative activity in comparison with the system in which either one of these substances is immobilized solely and the other is used in a solution state.

Then, the anticoagulative activities of the immobilized materials are compared without the heparin solution or the antithrombin III solution in the above mentioned procedure. That is, a designed amount of each of I-ATIII-HEP, I-ATIII and I-HEP is added to a thrombin solution, and after the mixture is shaken at 37° C. for a designed time, the remaining thrombin activity in the supernatant is determined by the coagulation time. By comparing the results, it is shown that, when the remaining thrombin activity of the control is regarded as 100%, the remaining thrombin activity in case of using I-ATIII is 10 to 20% and the remaining thrombin activity in case of using I-ATIII-HEP is 0.2 to 0.7% under the conditions in which the remaining thrombin activity in case of using I-HEP is 20%.

When I-ATIII-HEP is stored in an incubator at 37° C. for several weeks, no decrease of the antithrombin activity is observed, and a maximum effect is obtained only in 30 seconds in the reaction with a thrombin solution.

EXAMPLE 5

Each of I-ATIII-HEP, I-ATIII and I-HEP obtained in Example 1 (each 25 mg) is suspended in a buffer (50 mM Tris-HCl, 100 mM NaCl, 10 mM $CaCl_2$; pH 7.5) (500 μl), and a solution of the Xa factor (120 μl) is added thereto. The resulting mixture is allowed to stand at 37° C. for 3 or 5 minutes, and then I-ATIII-HEP, I-ATIII or I-HEP is removed therefrom. The resultant solution (100 μl) is added to a 0.1 mM synthetic substrate aqueous solution (1 ml) and allowed to stand at 37° C. for 20 minutes. After addition of a 17% acetate aqueous solution (1.5 ml), the remaining percentage of the Xa factor activity is measured by the use of a fluorophotometer. The results are shown in Table 4.

Table 4

| Immobilized material | Remaining percentage of Xa factor activity (%) | |
|---|---|---|
| | Reacted for 3 minutes | Reacted for 5 minutes |
| Control | 100 | 100 |
| I-HEP | 100 | 100 |
| I-ATIII | 71 | 53 |
| I-ATIII-HEP | 15 | 11 |

From this table, it is understood that I-ATIII-HEP exhibits a remarkable inhibitive activity against the Xa factor, while I-HEP does not show any inhibitive activity.

What is claimed is:

1. An artificial medical material with anticoagulative activity which comprises a carrier material with heparin and antithrombin III co-immobilized thereon.

2. An artificial medical material according to claim 1, wherein the carrier material is a water-insoluble high polymer.

3. An artificial medical material according to claim 2, wherein the water-insoluble high polymer is agarose.

4. An artificial medical material according to claim 2, wherein the water-insoluble high polymer is polyvinyl alcohol.

5. An artificial medical material according to claim 2, wherein the water-insoluble high polymer is polyhydroxyethyl methacrylate.

6. An artificial medical material according to claim 1, wherein the carrier material is activated carrier material.

7. An artificial medical material according to claim 6, wherein the carrier material is cyanogen-bromide-activated carrier material.

8. An artificial medical material according to claim 1, wherein the proportion of heparin and antithrombin III is from 1:1 to 10:1 (by weight).

9. An artificial medical material according to claim 1, wherein heparin and antithrombin III are immobilized on the carrier material, respectively, in amounts of from 1 to 50 mg per 1 g of the carrier material.

10. A method for prevention of coagulation of blood which comprises contacting the blood with an artificial medical material according to claim 1.

11. A method for inactivation of the Xa factor in blood which comprises contacting the blood with an artificial medical material according to claim 1.

12. In a method for prevention of coagulation of blood by contacting the blood with an artificial medical material bearing heparin immobilized thereon, the improvement wherein the artificial medical material also bears antithrombin III immobilized thereon so that the anticoagulative activity of heparin is greatly enhanced.

13. A combination of immobilized heparin and an anticoagulative-activity-enhancing amount of immobilized antithrombin III on a carrier material.

* * * * *